United States Patent
Carr

(12) 
(10) Patent No.: US 6,365,576 B1
(45) Date of Patent: Apr. 2, 2002

(54) METHOD FOR INHIBITING HERPES INFECTION

(75) Inventor: Daniel J. J. Carr, Edmond, OK (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/339,622

(22) Filed: Jun. 24, 1999

(51) Int. Cl.$^7$ .................. A61K 48/00; A61K 35/00; C12N 15/63; C12N 15/85

(52) U.S. Cl. .................. 514/44; 424/93.21; 435/320.1; 435/325; 435/455

(58) Field of Search .................. 514/44; 536/23.52; 424/93.21; 435/320.1, 325, 455

(56) References Cited

PUBLICATIONS

Noisakran et al. J Immunol 1999 Apr., 162:4184–4190.*
Encyclopaedia Britainnica online. Interferon.*
Robbins et al. Pharmacol Ther 1998; 1:35–47.*
He et al., "Kinetics of Cytokine Production in the Cornea and Trigeminal Ganglion of C57BL/6 Mice after Corneal HSV–1 infection." J. of Interferon and Cytokine Research, vol. 19: 609–615, 1999.*
Nussenblatt et al., "Perspectives on gene therapy in the treatment of oculuar inflammation." Eye, vol. 11: 217–221, 1997.*
Clay et al., "Potential Use of T cell receptor gene to modify hematopoietic stem cells for the gene therapy of cancer." Pathology Oncology Research, vol. 5 (1): 3–15, 1999.*
Verma et al., "Gene therapy–promises, problems, and prospects." Nature, vol. 389: 239–242, Sep. 1997.*
W. French Anderson. "Human gene therapy." Nature, vol. 392 (Supp): 25–30, Apr. 1998.*
Orkin et al., "Report and recommendations of the panel to assess the NIH investment in research on gene therapy." pp. 1–20, Dec. 1995.*
Carr, D. et al., "Astrocyte–targeted expression of IFN–α1 protects mice from acute ocular herpes simplex virus type I infection," J. Immunol., vol. 161, pp. 4859–4865 (1998).
Chun, S. et al., "Modulation of viral immunoinflammatory responses with cytokine DNA administered by different routes," J. Virol., vol. 72, pp. 5545–5551 (1998).

Dahesia, M. et al., "Suppression of ongoing ocular inflammatory disease by topical administration of plasmid DNA encoding IL–10," J. Immunol., vol. 159, pp. 1945–1952 (1997).
Horton, H. et al., "A gene therapy for cancer using intramuscular injection of plasmid DNA encoding interferon α," Proc. Natl. Acad. Sci. USA, vol. 96, pp. 1553–1558 (1999).
Klavinskis, L. et al., "Intranasal immunization with plasmid DNA–lipid complexes elicits mucosal immunity in the female genital and rectal tracts," J. Immunol., vol. 162, pp. 254–262 (1999).
Noisakran, S. et al., "Ectopic expression of DNA encoding IFN–α1 in the cornea protects mice from herpes simplex virus type 1–induced encephalitis," J. Immunol., vol. 162, pp. 4184–4190 (1999).
Yeow, W. et al., "Antiviral activities of individual murine IFNα subtypes in vivo: intramuscular injection of IFN expression constructs reduces cytomegalovirus replication," J. Immunol., vol. 160, pp. 2932–2939 (1998).

* cited by examiner

Primary Examiner—James Ketter
Assistant Examiner—Q. Janice Li
(74) Attorney, Agent, or Firm—John H. Runnels

(57) ABSTRACT

The topical administration of a plasmid encoding a Type I interferon such as interferon α1 (IFN-α1) to the cornea has potent anti-herpes activity. The expression of the interferon transgene in the corneas of infected individuals is transient and short-lived. The plasmid protected mice from HSV-1-induced encephalitis in a dose- and time-dependent manner when applied to the cornea prior to infection. The method may be used to treat or prevent herpes infections not only in the eye, but also in other portions of the oropharyngeal region, and in other mucous membranes including the genitalia. Patients presenting with acute or reactivated herpes infections are topically treated with DNA encoding a Type I interferon, where the DNA is not designed to integrate into the genome, but is placed under the control of a promoter that will cause expression of the interferon while the DNA persists in the cells that take it up. By limiting viral replication, the treatment reduces the initial spread of virus, and thereby also reduces the establishment of latent infections. The method provides a low-cost, non-invasive treatment for HSV infection that may either be administered by physicians or other health care personnel, or self-administered by patients.

5 Claims, No Drawings

METHOD FOR INHIBITING HERPES INFECTION

The development of this invention was funded by the Government under grant number NS35470 awarded by the National Institute of Neurological Disorders and Stroke. The Government has certain rights in this invention.

This invention pertains to the inhibition of herpes infections.

Herpes simplex virus type 1 (HSV-1) eye infections are very common in humans. Ocular herpes infections can have serious complications, including encephalitis, herpetic keratoconjunctivitis, and even blindness. Local immune responses to HSV-1 infection of the cornea include infiltration of mononuclear cells such as $CD4^+$ and $CD8^+$ T cells, macrophages, and neutrophils; the activation of natural killer cells; and the production of various cytokines. There are no successful HSV-1 vaccines commercially available today.

Next to trauma, the leading cause of blindness in the industrialized world is HSV infection. Approximately 6000 corneal transplants are conducted each year for patients with recurrent HSV infection. Ultimately, most of these patients lose their sight.

There are several subtypes of interferons. Type I interferons, such as IFN-α and IFN-β types, are naturally occurring hormones produced by the immune system and by non-immune cells in response to viral infections and other specific inducers. Endogenous type I interferons inhibit the replication of infectious virus in the host cells by destabilizing viral RNA, degrading viral nucleic acids, enhancing the expression of certain host proteins (e.g., MHC-I antigens), enhancing anti-viral effector mechanisms of the host immune system, and other anti-viral mechanisms. IFN-α has been used against established tumors and chronic viral infections (e.g., hepatitis B and C virus, AIDS-associated Kaposi's sarcoma). Herpes simplex virus type I ("HSV-1") is known to be sensitive to the anti-viral effects of IFN-α.

D. Carr et al., "Astrocyte-targeted expression of IFN-α1 protects mice from acute ocular herpes simplex virus type I infection," *J. Immunol.*, vol. 161, pp. 4859–4865 (1998)(not admitted to be prior art) discloses that transgenic mice having a gene encoding IFN-α1 in the germline, where the gene is under the control of an astrocyte-specific promoter, were more resistant to HSV-1 infection than were non-transgenic control mice.

Some gene therapy efforts have used vectors encoding cytokine genes. Following in vivo transfection with a gene therapy vector, host cells take up plasmid DNA encoding the gene of interest. In situ expression of the transgene either antagonizes the microbial infection or reduces the destructive inflammatory process associated with the infection.

M. Dahesia et al., "Suppression of ongoing ocular inflammatory disease by topical administration of plasmid DNA encoding IL-10, " *J. Immunol.*, vol. 159, pp. 1945–1952 (1997) disclosed that topical administration to the cornea of plasmid DNA encoding IL-10 reduced the incidence of herpetic stromal keratitis in mice; however, it was reported that similar effects were not seen with DNA encoding IL-2 and GM-CSF, the only other cytokine DNAs that had been tested to date.

W. Yeow et al., "Antiviral activities of individual murine IFN-α subtypes in vivo: intramuscular injection of IFN expression constructs reduces cytomegalovirus replication," *J. Immunol*, vol. 160, pp. 2932–2939 (1998) discloses the intramuscular injection of naked DNA plasmids coding for IFN-α1, IFN-α4, or IFN-α9 subtypes into the tibialis anterior muscles of mice, followed by challenge with murine cytomegalovirus. Mice injected with the IFN-α plasmids showed lower CMV titers than did controls, with the lowest titers reported for the IFN-α1 DNA treatment.

S. Chun et al., "Modulation of viral immunoinflammatory responses with cytokine DNA administered by different routes," *J. Virol.*, vol. 72, pp. 5545–5551 (1998) discloses that the systemic or topical administration of IL4 and IL-10 DNA, but not IL-2 or IFN-γ DNA, suppressed HSV-specific, delayed-type hypersensitivity in mice. Inflammatory lesions associated with corneal HSV infection were suppressed by administering IL4 and IL-10 DNA to nasal mucosa or ocular surfaces.

H. Horton et al., "A gene therapy for cancer using intramuscular injection of plasmid DNA encoding interferon α," *Proc. Natl. Acad. Sci. USA*, vol. 96, pp. 1553–1558 (1999) discloses that the intramuscular injection of a plasmid encoding murine interferon-α in mice had significant anti-tumor effects.

I have discovered that the topical administration of a plasmid encoding interferon α1(IFN-α1) to the cornea has potent anti-herpes activity. The expression of the IFNα1 transgene in the corneas of infected individuals is transient and short-lived. The plasmid protected mice from HSV-1-induced encephalitis in a dose- and time-dependent manner when applied to the cornea prior to infection. The protective effect was mediated through the expression of the transgene rather than exposure to plasmid DNA, as indicated in experiments using neutralizing antibody to IFN-α/β. Gene therapy by delivery of a transgene in a plasmid should be qualitatively safer than the use of virus vectors, due to the lower potential for adverse effects.

The novel method may be used to treat or prevent herpes infections not only in the eye, but also in other portions of the oropharyngeal region, and in other mucous membranes including the genitalia. Patients presenting with acute or reactivated HSV-1 or other herpes infections are topically treated with DNA (e.g., a plasmid) encoding a type I interferon such as interferon-α1 ("IFN-α1"), where the DNA is not designed to integrate into the genome, but is placed under the control of a promoter that will cause expression of the interferon while the DNA persists in the cells that take it up.

Viral replication may be inhibited by targeting constitutive but transient expression of type I IFN genes to cells infected by herpes virus. In particular, the experimental results reported here show that the transgene blocks viral replication by antagonizing the expression of immediate early and early viral genes that are necessary for productive infection. The transgene up-regulates the expression of MHC-I antigen by the transfected tissue, facilitating the presentation of viral antigen to the immune system, and subsequently targeting infected cells for destruction by immune effector cells.

The novel method may be used either independently, or in conjunction with other antiviral therapies, such as acyclovir or ganciclovir.

By limiting viral replication, the novel treatment reduces the initial spread of virus, and thereby also reduces the establishment of latent infections. Typically, most morbidity from an HSV-1 infection occurs when latently-infected cells (neurons that are infected with the virus, but that for a time do not express any viral antigens or produce infectious virus) reactivate in response to environmental cues. Tissue destruction then results as host immune cells respond to the reactivated virus and destroy the infected cells. Patients with recurrent reactivation of latent HSV-1 can, for example, lose their sight or experience various autoimmune diseases indirectly triggered by the virus. HSV reactivation plagues approximately 20% of infected individuals, some of which become serious cases of reactivation.

The novel method of treating HSV infection may be used to control ocular and other HSV infections. The plasmid construct (DNA only) is placed in a sterile solution with appropriate buffers to optimize in situ transfection of target tissue. For example, we have placed the plasmid in phosphate buffered saline (pH 7.4) at a concentration of 33.3 $\mu g/\mu l$. We have found that the plasmid construct is stable in this storage medium for about 10 days. It then begins to degrade, with little or no efficacy remaining after 21 days.

DNA purification resins such as are known in the art are used to minimize endotoxin contamination of the plasmid DNA. The solution is applied to the target tissue (e.g., the eyes) topically, typically~3 $\mu l$ volume. As discussed below, the results of initial animal tests were quite promising. This construct or analogous constructs will therefore be tested in humans for efficacy against HSV-1 in compliance with pertinent laws and regulations.

This invention provides a low-cost, non-invasive treatment for HSV infection that may either be administered by physicians or other health care personnel, or self-administered by patients. An important benefit of the present invention is its strong inhibition of latent infections if applied during the acute phase of infection. Reactivation should therefore be greatly reduced. The application of exogenous interferons has previously been shown to be non-protective against re-exposure to virus, since it does not lead to the mounting of an active immune response. However, the novel transgene approach leads to the mounting of a substantial humoral immune response, a response that is essentially identical to the immune response shown by individuals who survive the initial infection and mount a significant adaptive immune response to the virus.

MATERIALS AND METHODS

Virus and Cells

Vero and CV-1 African green monkey kidney cell lines were obtained from the American Type Culture Collection (Rockville, Md.), accession numbers CCL81.1 and CCL70, respectively. Cells were cultured in RPMI-1640 medium (Irvine Scientific, Santa Ana, Calif.) supplemented with 5% fetal bovine serum (FBS) (Gibco BRL, Gaithersburg, Md.) and an antibiotic/antimycotic solution (Gibco BRL) in an atmosphere of 37° C., 5% $CO_2$, and 95% relative humidity. HSV-1 (McKrae) stock was prepared as described in W. Halford et al., "Persistent cytokine expression in trigeminal ganglion latently infected with herpes simplex virus type 1," *J. Immunol.*, vol. 157, pp. 3542ff. (1996).

Plasmid DNA Construct

Plasmid pCMV-β (vector) was purchased from Clontech Laboratories, Inc. (Palo Alto, Calif.). This 7.2-kb eukaryotic expression vector contains an *E. coli* β-galactosidase reporter gene under the control of the human cytomegalovirus (CMV) immediate early promoter/enhancer, an RNA splice donor and acceptor sequence, and the SV40 late polyadenylation signal. The CMV promoter was chosen for its systenic expression. Other systemically-expressed promoters, or promoters that cause expression only in the tissue of interest may be used instead. A coding segment for IFN-α1 was inserted, and a portion of the 3' non-coding segment was deleted, as its retention could reduce the stability of the cytokine transgene.

Plasmid pCMV-IFNα1 was generated as follows. A 690 bp HindIII-EcoRI fragment of mouse IFNα1 cDNA (a kind gift from Dr. E. Zwarthoff, Erasmus University, Rotterdam, The Netherlands) was excised from pGEM-4. After ligation to NotI linkers, this fragment was cloned into the NotI site of pCMV-β. The new plasmid DNA constructs were then transformed into Short™ INVαF'-competent *E. coli* cells according to the manufacturer's instructions (Invitrogen Corporation, San Diego, Calif.). The large scale production and purification of DNA from these transformed *E. coli* was as described in J. Sambrook et al in C. Nolan et al. (Eds.)*Molecular Cloning: A Laboratory Manual*, Vol. 1, pp. 1.33ff(1989) with minor modifications.

Administration of Plasmid DNA Construct

Mice were anaesthetized, and their corneas were scarified with a 25 g needle and blotted with tissue. Then 100 $\mu g$/eye of either pCMV-β vector (control) or pCMV-IFNα1 was applied topically 24 hr, 72 hr, or 2 wk prior to HSV-1 injection. In addition, to test the prophylactic effect of the IFNα1 construct on acute HSV-1 infection, HSV-1 infected mice were anaesthetized and their eyes were topically treated in the same manner with 100 $\mu g$/eye of either pCMV-β or pCMV-IFNα1 at 24 hr post-infection. For the dose response study, mice were treated with either PBS or pCMV-IFNα1 (5, 25, 50, or 100 $\mu g$/eye), and were then infected with 450 PFU/eye of HSV-1 24 hr later.

Infection of Mice

Female ICR mice (25–34 g, Harlan-Sprague Dawley, Indianapolis, Ind.) were anesthetized by intraperitoneal injection of 0.1 ml of PBS containing xylazine (2 mg/ml concentration, administered at the rate of 6.6 mg/kg body mass) and ketamine (30 mg/ml; 100 mg/kg). Corneas were scarified with a 25 g needle, and tear film was blotted with tissue. Mice were inoculated with 450 plaque forming units of HSV-1 (McKrae strain) per eye. Infection was verified by swabbing the eyes 2–3 days post infection (PI) and placing the swabs in CV-1 African green monkey kidney cell monolayer cultures to observe for cytopathic effect.

Animals were handled in accordance with the National Institutes of Health guidelines on the Care and Use of Laboratory Animals, publication no. 85-23, revised 1996. All procedures were approved by the Louisiana State University Medical Center Institutional Animal Care and Use Committee.

Reverse Transcription (RT)-PCR

RT-PCR was performed as described in W. Halford et al., "Persistent cytokine expression in trigemnal ganglion latently infected with herpes simplex virus type 1," *J. Immunol.*, vol. 157, pp. 3542 ff(1996). Briefly, RNA was extracted from excised tissue in Ultraspec RNA isolation reagent (Biotecx, Houston, Tex.). First-strand cDNA was synthesized using avian myeloblastosis virus reverse transcriptase (Promega, Madison, Wis.). PCR was performed in a thermal cycler (Ericomp Delta cycler, Ericomp, San Diego, Calif.) for 30–35 cycles of 94° C. (1 min, 15 sec), 57–65° C. (1 min 15 sec), 72° C. (30–45 sec). PCR primers for glyceraldehyde-3-phosphate dehydrogenase (GAPDH), latency associated transcript (LAT) RNAs, infected cell polypeptide (ICP)27, IFN-γ, IL-6, and IL-10 were as described in W. Halford et al., "Persistent cytokine expression in trigeminal ganglion latently infected with herpes simplex virus type 1," *J. Immunol*, vol. 157, pp. 3542ff (1996); and J. Daigle et al., "Androstenediol antagonizes herpes simplex virus type 1-induced encephalitis through the augmentation of type I IFN production," *J. Immunol.*, vol. 160, pp. 3060ff (1998). IFN-α (consensus sequence for IFNα1, 2, and 7), CD4, and CD8 primer sequences were obtained from Clontech Laboratories, Inc. (Palo Alto, Calif.). Primers for viral protein (VP)16 were 5'-GGACTCGTATTCCAGCTTCAC-3' (sense) (SEQ. ID NO. 1) and 5'-CGTCCTCGCCGTCTAAGTG-3' (antisense) (SEQ. ID NO.2). Primers for thymidine kinase (TK) were 5'-ATGGCTTCGTACCCCTGCCAT-3' (sense)(SEQ. ID NO. 3) and 5'-GGTATCGCGCGGCCGGGTA-3' (antisense) (SEQ. ID NO. 4). Primers specific for the IFN-α1 transgene were 5'-ATTCCCGCAGGAGAAGGTGGATGCCCCA-3' (sense)(SEQ. ID NO. 5) and 5'-GAGTAGTTACATAGAATAGTACA-3' (antisense) (SEQ. ID NO. 6) based on the published sequence for the murine IFN-α1 cDNA sequence upstream primer starting at nucleotide 550 (Genbank accession no. X01974) The downstream primer sequence starting at nucleotide 20 of the SV-40 late region polyadenylation sequence was used as a 3' UTR in the pCMV-IFNα1 fusion gene construct (sequence according to Clontech Laboratories, Inc.). Primers for JE/monocyte chemoattractant protein-1 (MCP-1) and the setting for the amplification of the specific products were as described Y. Su et al, "Protective antibody therapy is associated with reduced chemokine transcripts in herpes simplex virus type 1 corneal infection," *J. Virol.*, vol. 70, pp. 1277ff (1996). Primers for cytokine response gene (CRG)-2 were 5'-CAGCACCATGAACCCAAGTGC-3' (sense)(SEQ. ID NO.7) and 5'-GCTGGTCACCTTTCAGAAGACC-3' (antisense)(SEQ. ID NO. 8).

Northern Analysis

For Northern blot hybridization, total RNA (5 µg) was denatured, electrophoresed in 1% agarose/2.2 M formaldehyde gels, transferred to nylon membranes, and hydridized overnight at 45° C. with $^{32}$P-labeled cDNA probes. The probes used were a 0.6 kb, Kpn 1-Sac I fragment of a murine MHC-class (H2D$^b$) cDNA (provided by Dr. P. Petersen, Scripps Research Institute, La Jolla, Calif.); and a 0.26 kb fragment of the murine β-actin gene as described in K. Tokunaga et al., "Nucleotide sequence of a full-length cDNA for mouse cytoskeletal beta-actin mRNA," *Nucleic Acid Res.*, vol. 14, pp. 829ff(1986). For quantification, autoradiographs were scanned (Scanjet 4C/T, Hewlett Packard, San Jose, Calif.), and band densities were assessed with NIH image 1.57 software.

In Vivo Neutralization Assay

In indicated experiments, mice received rabbit anti-mouse anti-IFN-α/β (Access Biomedical, San Diego, Calif.; 1000 neutralizing U) or normal rabbit Ig at the time of infection and 3 and 6 days PI as described in Y. Su et al., "Protective antibody therapy is associated with reduced chemokine transcripts in herpes simplex virus type 1 corneal infection," *J. Virol.*, vol. 70, pp. 1277ff(1996).

Statistics

The Mann-Whitney U test was used to determine significant (p<0.05) differences in cumulative survival between the IFN-α1 plasmid construct and the vector construct-treated groups using the GBSTAT program (Dynamic Microsystems, Silver Springs, Md.). All other statistical analyses comparing vehicle- or vector-treated mice to the IFNα1 construct-treated animals were performed by ANOVA and Tukey's post hoc t-test.

RESULTS

Transient Expression of Plasmid DNA Encoding IFN-α1 in eyes.

To verify the expression of exogenous IFN-α1 in the eyes, either 100 µg/eye of pCMV-β (vector control) or of pCMV-IFNα1 were topically administered to mice (n=2/experiment, repeated three times) 24 hr, 72 hr, or 2 weeks before sacrifice. RNA isolation and RT-PCR for glyceraldehyde-s-phosphate dehydrogenase (GAPDH, control) and for the IFN-α1 transgene were performed from tissue extracted from the eyes of individual animals. RNA for the GAPDH control was found at all times. However, the transgene for IFN-α1 was expressed in uninfected eyes in a time-dependent manner as determined by RT-PCR and ribonuclease protection assay. Likewise, in IFN-α1 construct-treated mice infected 24 hours later, IFN-α1 transgene expression was detected in the eyes 3 days PI (n=3/experiment, repeated three times), but was absent in the vector-treated mice. However, expression during infection was transient, disappearing by 6 days PI. A possible explanation is that the transfected host corneal epithelial cells were compromised or destroyed as a result of the infection, leading to a loss of transgene expression during the acute phase of the infection.

In Vivo Transfection with Plasmid DNA Encoding IFN-α1 Protected Mice Against Ocular HSV-1 Challenge.

To determine the in vivo efficacy of the IFN-α1 plasmid construct against ocular HSV-1 infection, 100 µg/eye of either pCMV-β (vector) or pCMV-IFN-β1 were topically applied to the corneas of mice at 24 hr, 72 hr, and 14 days prior to ocular HSV-1 infection, or at 24 hr PI. Topical administration of pCMV-IFNα1 24 hr prior to infection significantly (p<0.05) enhanced the cumulative survival of mice as compared to vector-treated mice. See Table 1.

TABLE 1

| Days Post Infection | pCMV-β (vector) | pCMV-IFN-α1 two weeks before infection | pCMV-IFN-α1 72 hours before infection | pCMV-IFN-α1 24 hours before infection | pCMV-IFN-α1 24 hours after infection |
|---|---|---|---|---|---|
| 5 | 100 | 100 | 100 | 100 | 100 |
| 6 | 92 | 100 | 100 | 100 | 100 |
| 7 | 62 | 90 | 90 | 90 | 80 |
| 8 | 37 | 54 | 70 | 60 | 60 |
| 9 | 24 | 37 | 40 | 50* | 50 |
| 10 | 10 | 17 | 30 | 50* | 30 |
| 11 | 5 | 17 | 20 | 50* | 30 |
| 12 | 5 | 17 | 20 | 50* | 30 |
| 13 | 5 | 0 | 20 | 50* | 30 |
| 14 | 5 | 0 | 20 | 50* | 30 |
| 30 | 5 | 0 | 20 | 50* | 30 |

In Table 1, the results given are for percentages of infected mice observed to survive at the listed times. Results represent 2–3 experiments (n=4–5/experiment) for pCMV-IFNα1 given at 24 hr, 72 hr, or 2 before HSV-1 infection; or at 24 hr following HSV-1 infection; and represent 4 experiments for pCMV-β (n=8–10/experiment). * p<0.05 compared to vector.

However, no statistically significant effect was seen for mice treated with the IFN-α1 construct 72 prior to infection or 24 hr following HSV-1 infection. None of the mice receiving the IFN-α1 construct two weeks prior to challenge survived until two weeks post-infection. These data demonstrate that, as expected, the construct's protective effect was transient.

To determine the dose-dependent efficacy of the IFNα1 construct against HSV-1, mice were topically given either vehicle (PBS) or pCMV-IFNα1 (5, 25, 50, or 100 µg/eye), and were challenged 24 hr later with HSV-1. Mice receiving higher concentrations of pCMV-IFNα1 (25–100 µg/eye) were significantly better protected against HSV-1 infection as compared to mice receiving vehicle (PBS) or pCMV-IFNα1 (5 µg/eye). See Table 2.

TABLE 2

The IFN-α1 Transgene Protected Mice From Ocular HSV-1 Infection in a Dose-Dependent Fashion[a]

| | | Treatment (IFNα1) | | | |
|---|---|---|---|---|---|
| Days Post-Infection | Vehicle (PBS) | 5.0 µg/eye | 25.0 µg/eye | 50.0 µg/eye | 100.0 µg/eye |
| 5 | 9/9[b] | 9/9 | 9/9 | 9/9 | 9/9 |
| 6 | 8/9 | 9/9 | 8/9 | 9/9 | 8/9 |
| 7 | 4/9 | 8/9 | 7/9 | 8/9 | 7/9 |
| 8 | 4/9 | 5/9 | 6/9 | 8/9 | 7/9 |
| 9 | 2/9 | 3/9 | 5/9* | 6/9 | 7/9* |
| 10 | 1/9 | 2/9 | 5/9* | 6/9* | 6/9* |
| 11 | 1/9 | 2/9 | 4/9* | 6/9* | 6/9* |
| 12 | 1/9 | 2/9 | 4/9* | 6/9* | 6/9* |
| 30 | 1/9 | 2/9 | 4/9* | 6/9* | 6/9* |

[a] Mice (n = 3/group/experiment; three experiments) were administered 3.0 µl of PBS or PBS containing the indicated amount of the IFN-α1 construct 24 hr prior to infection with HSV-1 (450 pfu/eye). Mice were monitored for survival.
[b] Numbers indicate: surviving animals/total number tested. This table is a summary of three separate experiments.
*$p < 0.05$, comparing the experimental group to the vehicle-treated controls, as determined by Mann-Whitney U test.

Effect of the IFN-α1 Construct on the Expression of MHC Transcripts, Viral Transcripts, Immune Cell Transcripts, Cytokine Transcripts, and Chemokine Transcripts.

Type I interferons have several anti-viral effects, including the induction or up-regulation of MHC class I molecules, which in turn facilitates CTL recognition of virally-infected cells. To determine whether application of the IFNα1 transgene onto the cornea elicited such an effect, mouse eyes (n=2/group) were transfected with 100 µg/eye of the pCMV-β vector or pCMV-IFNα1, and were then sacrificed 24 hr. post-treatment, and assessed for MHC class I mRNA expression. The results showed a five-fold increase in the expression of MHC class I RNA in eyes transfected with the IFNα1 transgene as compared to the vector-treated control group. Equivalent amounts of RNA for each sample were analyzed, using an assay for β-actin RNA as a control.

To further characterize the protective mechanism elicited by the IFN-α1 construct, viral loads were assessed in the eyes and in trigeminal ganglia (TG) during acute infection. There was a significant reduction in the amount of infectious virus recovered from the eyes of mice topically treated with the pCMV-IFNα1 as compared to the vector-treated controls 3 and 6 days PI. See Table 3. Similarly, 7 of 12 mice treated with the vector had detectable virus in the cerebellum (100 PFU/cerebellum), compared with 3 of 12 mice treated with the pCMV-IFNα1 construct (10 PFU/cerebellum).

TABLE 3

Viral Loads in Eyes and Trigeminal Ganglia

| Tissue Source and Treatment | Day 3 Post-Infection | Day 6 Post-Infection |
|---|---|---|
| Eyes, pCMV-β | 10,390 ± 3,258 | 784 ± 254 |
| Eyes, pCMV-IFN-α1 | 2,350 ± 927* | 101 ± 67* |
| TG, pCMV-β | 3,240 ± 140 | 5,144 ± 2559 |
| TG, pCMV-IFN-α1 | 125 ± 79 | 359 ± 110 |

In the experiments reported in Table 3, mice were topically treated with 100 µg/eye of either pCMV-β or pCMV-IFNα1, and were then infected with HSV-1 24 hr later. The viral loads in the eyes and the TGs were determined 3 and 6 days PI as previously described. Results are reported as mean ±SEM from 5 experiments; n=3 mice/experiment (pCMV-β) and n=3 mice/experiment (pCMV-IFNα1). *$p<0.05$ comparing the pCMV-IFNα1-treated group to the vector-treated control group.

We also observed that viral transcript expression was modified by the construct. Specifically, treatment with the IFN-α1 construct reduced expression of HSV-1 ICP27 and HSV-1 VP16 in the TG 3 days PI, while expression of thymidine kinase ("TK") was not detected. In the eye, HSV-1 TK was not detected in the pCMV-IFNα1-treated cornea. Topical administration of the IFN-α1 construct at day 6 PI reduced the expression of all viral transcripts tested (ICP27, TK, and VP 16), both in the eyes and in the TG.

Since cytokines and chemokines have been reported in the eyes and the TG during an acute ocular HSV-1 infection, and since the antigenic stimulus (in the form of infectious virus) is reduced in the pCMV-IFNα1-treated mice, we measured cytokine and chemokine transcript levels as well. We observed that application of the pCMV-IFNα1 construct 24 hr prior to infection reduced the expression of cytokine response gene 2 ("CRG-2") in the TG, CD8 and monocyte chemotactic protein 1 ("MCP-1") in the eyes, and IL-6 in both the eyes and the TG 3 days PI. The expression of MCP-1 in the TG was unchanged following treatment with the IFN-α1 construct. CD8 expression was not detected in the TG in either vector-treated or IFN-α1-treated mice 3 days PI. Later, 6 days PI during acute infection, topical administration of the IFNα1 construct resulted in reduced expression of IL-10 and CD8 in the TG. The expression of IL-6 in the TG was also reduced in the IFNα1 construct-treated mice. No other transcripts measured were found to differ significantly between the vector- and IFN-α1 construct treated mice day 6 PI.

Anti-IFN-α/β Antibody Blocked the Protective Effect Otherwise Elicited by the IFNα1 Construct.

To further demonstrate that the protective effect elicited by the transgene was due to IFNα, rather than the induction of an immune response to the plasmid DNA, neutralizing antibody to IFN-α/β or control rabbit immunoglobulin was administered to mice undergoing transgene administration. The pCMV-IFNα1-treated mice who were given the control antibody showed increased cumulative survival as compared to the vehicle-treated group. However, the pCMV-IFNα1-treated mice who were given the anti-IFN-α/β succumbed to the infection at the same rate as the untreated group of mice. See Table 4.

TABLE 4

| Days Post-Infection | No Treatment (saline) | Isotypic, control antibody | Anti-IFN-α/β antibody |
|---|---|---|---|
| 4 | 100 | 100 | 100 |
| 5 | 93 | 90 | 93 |
| 6 | 77 | 87 | 80 |
| 7 | 63 | 80 | 73 |
| 8 | 48 | 80 | 60 |
| 9 | 28 | 73* | 47 |
| 10 | 22 | 60* | 27 |
| 30 | 22 | 60* | 27 |

In the experiments reported in Table 4, mice were administered PBS or PCMV-IFNα1 (100 µ/eye) 24 hr prior to infection with HSV-1 (450 pfu/eye). At the time of infection, and again 3 and 6 days PI, mice (n=5/group/experiment; two replicate experiments) were given an intraperitoneal injection of anti-IFN-α/β or rabbit control antibody. Mice were monitored and recorded for survival. *$p<0.05$ comparing control Ig-treated mice with the control saline-treated mice on day 9 PI; and comparing control Ig-treated mice with the saline- and the control Ig-treated groups on days 10–30 PI.

Topical Administration of the IFN-α1 Construct Suppressed HSV-1 Reactivation.

To determine the effect of topical administration of naked plasmid DNA on HSV-1 latency and reactivation, TG explant co-cultures were established from HSV-1 infected mice that had survived into viral latency (i.e., day 30 PI). The results showed that the TGs from mice that had been given the IFN-α1 construct either at 72 hr prior to infection or at 24 hr after infection reactivated to levels similar to those for the vector control. However, none of the TGs from the mice who had been treated with the IFN-α1 construct 24 hr prior to infection reactivated (FIG. 7). See Table 5.

TABLE 5

| Days Post-Transplant | pCMV-β (vector), n = 4 | pCMV-IFN-α1 72 hours before infection, n = 4 | pCMV-IFN-α1 24 hours before infection, n = 16 | pCMV-IFN-α1 24 hours after infection, n = 6 |
| --- | --- | --- | --- | --- |
| 1  | 0  | 0  | 0 | 0  |
| 2  | 0  | 0  | 0 | 0  |
| 3  | 0  | 0  | 0 | 0  |
| 4  | 0  | 25 | 0 | 0  |
| 5  | 0  | 25 | 0 | 0  |
| 6  | 0  | 25 | 0 | 17 |
| 7  | 25 | 25 | 0 | 17 |
| 8  | 25 | 25 | 0 | 17 |
| 9  | 25 | 25 | 0 | 33 |
| 10 | 25 | 50 | 0 | 33 |
| 11 | 25 | 50 | 0 | 50 |

In the experiments reported in Table 5, trigeminal ganglia were obtained from mice 30 days PI and were co-cultured with CV-1 indicator cells to observe for cytopathic effects. Supernatants from the cultures were collected daily for 11 days and assessed for infectious virus by plaque assay using CV-1 cells; n=4 (PCMV-β or pCMV-IFNα1 treatment at 72 hr before infection), n=6 (pCMV-IFNα1 treatment at 24 after infection), n=16 (pCMV-IFNα1 treatment at 24 before infection).

Following this 11 day survey, cultures were collected and assayed for LAT and GAPDH (control) expression by RT-PCR. Latency-associated RNA transcripts ("LATs") were weakly expressed in the TGs from non-reactivated explant cultures from mice pretreated with pCMV-IFNα1 24 hr prior to infection, as determined by RT-PCR compared to samples from mice treated with the transgene PI or as compared to vector-treated mice. The presence of the transgene appeared to reduce the establishment of latent HSV-1 in the sensory ganglia.

DISCUSSION

The experimental data reported above showed that transient expression of IFN-α1 in the eye reduced viral replication as evidenced by a reduction in the viral load and expression of viral genes during the course of acute infection. Placing the IFN-α1 transgene in the eye prior to infection inhibited the replication and spread of the virus from the origin of infection (cornea) to the sensory ganglia, and apparently to the central nervous system as well: Viral loads in the cerebellum showed a reduction in HSV-1 at 6 days PI.

The natural immune response to acute HSV infection itself produces significant pathology. The reduction in viral replication and spread produced by constructs in accordance with the present invention can substantially reduce the inflammation otherwise caused by HSV infection. For example, we found a reduction in some chemokines (MCP-1 and CRG-2), cytokines (IL-6 and IL-10), and immune cell (CD8) transcripts in the eyes and TGs of treated mice. Since IL-10 may reduce the levels of IFNα1 that would otherwise be induced by HSV infection, the transgene may also help fight viral infection by reducing IL-10 levels that could otherwise suppress endogenous production of virally-induced IFNα.

One mechanism HSV-1 uses to elude immune surveillance is to block antigen processing and presentation by infected cells. The IFN-α1 transgene- induced increase in the expression of class I MHCs within the eye coincided with increased resistance to HSV-1 infection. Another means by which the pCMV IFNα1 construct may increase resistance to HSV-1 infection may therefore be by enhancing the expression of MHC class I in the eye, thus increasing antigen presentation.

In addition to protecting against acute HSV-1 infection, topical administration of the IFN-α1 construct 24 hr prior to infection reduced HSV latency.

Although the transgene was delivered in the prototype experiments reported here by bolus administration of DNA, it is possible that multiple administrations of the DNA over time will provide greater total levels of protection. On the other hand, one advantage to a single administration is that decreased expression of the transgene will reduce host immune response to the product. Recent findings by some researchers in other contexts have suggested that multiple exposure to plasmid DNA containing transgenes encoding chemokines can induce a humoral immune response to the transgene product, although the mechanism underlying this response is currently unknown.

In lieu of delivering a construct in accordance with this invention as naked plasmid DNA, the construct could also be delivered by any one of several delivery systems known in the art, such as via liposomes. The delivery system itself should not provoke an immune response; thus delivery by a viral vector is not preferred.

This invention will work with other herpes viruses as well as HSV-I, such as herpes simplex II, varicella zoster virus, pseudorabies, bovine herpes virus, equine herpes virus, and Marek's disease. For example, preliminary data showed that the type I IFN transgenes were effective in treating vaginal HSV-2 infections in mice. The preliminary data showed that a significant degree of protection was afforded to animals treated post-HSV-2-infection, measuring mortality as the endpoint.

This invention will work with genes encoding other Type I interferons, including the several classes of IFN-α and of IFN-β. For example, preliminary data showed that transgenes encoding IFN-β provided a similar degree of efficacy against ocular herpes.

The complete disclosures of all references cited in this specification are hereby incorporated by reference, as is the complete disclosure of the following paper, which is not prior art to the present application: S. Noisakran et al., "Ectopic expression of DNA encoding IFN-α1 in the cornea protects mice from herpes simplex virus type 1-induced encephalitis," *J. Immunol.*, vol. 162, pp. 4184–4190 (1999). In the event of an otherwise irreconcilable conflict, however, the present specification shall control.

I claim:

1. A method for transiently inhibiting herpes virus infection in a cornea, comprising topically administering to the cornea a DNA sequence that encodes interferon α1, and a promoter operatively linked to the DNA sequence; wherein the promoter induces constitutive expression of the DNA sequence; wherein the DNA sequence and the promoter are not contained in a virus; whereby cells of the cornea express interferon α1, thereby transiently inhibiting herpes virus infection in the cornea.

2. A method as recited in claim 1, wherein the promoter is the human cytomegalovirus immediate early promoter.

3. A method as recited in claim 1, wherein the DNA sequence encodes human interferon α1.

4. A method as recited in claim 3, wherein the promoter is the human cytomegalovirus immediate early promoter.

5. A method as recited in claim 1, wherein the DNA sequence and the promoter are contained in a plasmid.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 1
ggactcgtat tccagcttca c                                              21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 2
cgtcctcgcc gtctaagtg                                                 19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 3
atggcttcgt acccctgcca t                                              21

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 4
ggtatcgcgc ggccgggta                                                 19

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 5
attcccgcag gagaaggtgg atgcccca                                       28

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 6
gagtagttac atagaatagt aca                                            23

<210> SEQ ID NO 7
<211> LENGTH: 21

```
<212> TYPE: DNA
<213> ORGANISM: Artificial Sequence
<220> FEATURE:
<223> OTHER INFORMATION: Description of Artificial Sequence: PCR Primer

<400> SEQUENCE: 7
cagcaccatg aacccaagtg c                                        21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 8
gctggtcacc tttcagaaga cc                                       22
```